US00PP24658P3

(12) United States Plant Patent
Rateau

(10) Patent No.: US PP24,658 P3
(45) Date of Patent: Jul. 22, 2014

(54) FLORIBUNDA ROSE PLANT NAMED 'EVANRAT'

(50) Latin Name: *Rosa hybrida*
Varietal Denomination: Evanrat

(75) Inventor: Jérôme Rateau, Pithiviers (FR)

(73) Assignee: LVMH Recherche, Saint Jean de Braye (FR)

( * ) Notice: Subject to any disclaimer, the term of this patent is extended or adjusted under 35 U.S.C. 154(b) by 12 days.

(21) Appl. No.: 13/385,337

(22) Filed: Feb. 14, 2012

(65) Prior Publication Data

US 2012/0210471 P1 Aug. 16, 2012

(30) Foreign Application Priority Data

Feb. 14, 2011 (QZ) ..... PBR A201100150

(51) Int. Cl.
*A01H 5/00* (2006.01)

(52) U.S. Cl.
USPC ..... Plt./148

(58) Field of Classification Search
USPC ..... Plt./148, 141, 149
See application file for complete search history.

*Primary Examiner* — Kent L Bell
(74) *Attorney, Agent, or Firm* — Porzio, Bromberg & Newman, P.C.

(57) ABSTRACT

A new and distinct variety of Floribunda rose plant is provided that forms in abundance on a substantially continuous basis attractive double blossoms that are light pink in coloration. The buds are pointed and oval in configuration. The vegetation is strong and vigorous and a rounded and bushy growth habit is displayed. The ornamental foliage is dark green with a glossy upper surface and contrasts well with the light pink blossoms. The plant is particularly well suited for providing attractive ornamentation.

4 Drawing Sheets

Botanical/commercial classification: *Rosa hybrida*/Floribunda Rose Plant. Varietal denomination: cv. Evanrat.

CROSS-REFERENCE TO RELATED APPLICATION

This application claims priority to CVPO Application No. A201100150.

Inventors: Jerome Rateau (Les Roses Anciennes Andre Eve, FR)

SUMMARY OF THE INVENTION

The new variety of *Rosa hybrida* Floribunda rose plant was created in France by artificial pollination wherein two parents were crossed which previously had been studied in the hope that they would contribute the desired characteristics. The female parent (i.e., the seed parent) was the 'Auscent' variety. The male parent (i.e., the pollen parent) was the 'Dorblan' variety.

The seeds resulting from the above pollination were sown and small plants were obtained which were physically and biologically different from each other. Selective study resulted in the identification of a single plant of the new variety.

It was found that the new Floribunda rose plant of the present invention: (a) exhibits a rounded and bushy growth habit, (b) forms strong and vigorous vegetation, (c) abundantly and substantially continuously forms attractive double light pink blossoms, (d) displays attractive ornamental glossy dark green foliage, and (e) is particularly well suited for providing attractive ornamentation.

The new variety well meets the needs of the horticultural industry. It can be grown to advantage as attractive ornamentation in parks, gardens, public areas, and residential settings. The light pink blossoms contrast nicely with the glossy dark green foliage.

The new variety can be readily distinguished from its ancestors. For instance, the 'Auscent' variety is a Floribunda type that bears semi-double informally cupped medium pink flowers, lacking fragrance. The 'Dorblan' variety is a Hybrid Tea that forms very fragrant white flowers with curly petals.

The new variety has been found to undergo asexual propagation in France, by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Evanrat'.

BRIEF DESCRIPTION OF THE PHOTOGRAPH

The accompanying photographs show, as nearly true as it is reasonably possible to make the same in a color illustration of this character, typical blossoms of the new variety. The depicted plant was approximately three years of age and was being grown outdoors during June 2010 at Pithiviers (France).

Figure 1:
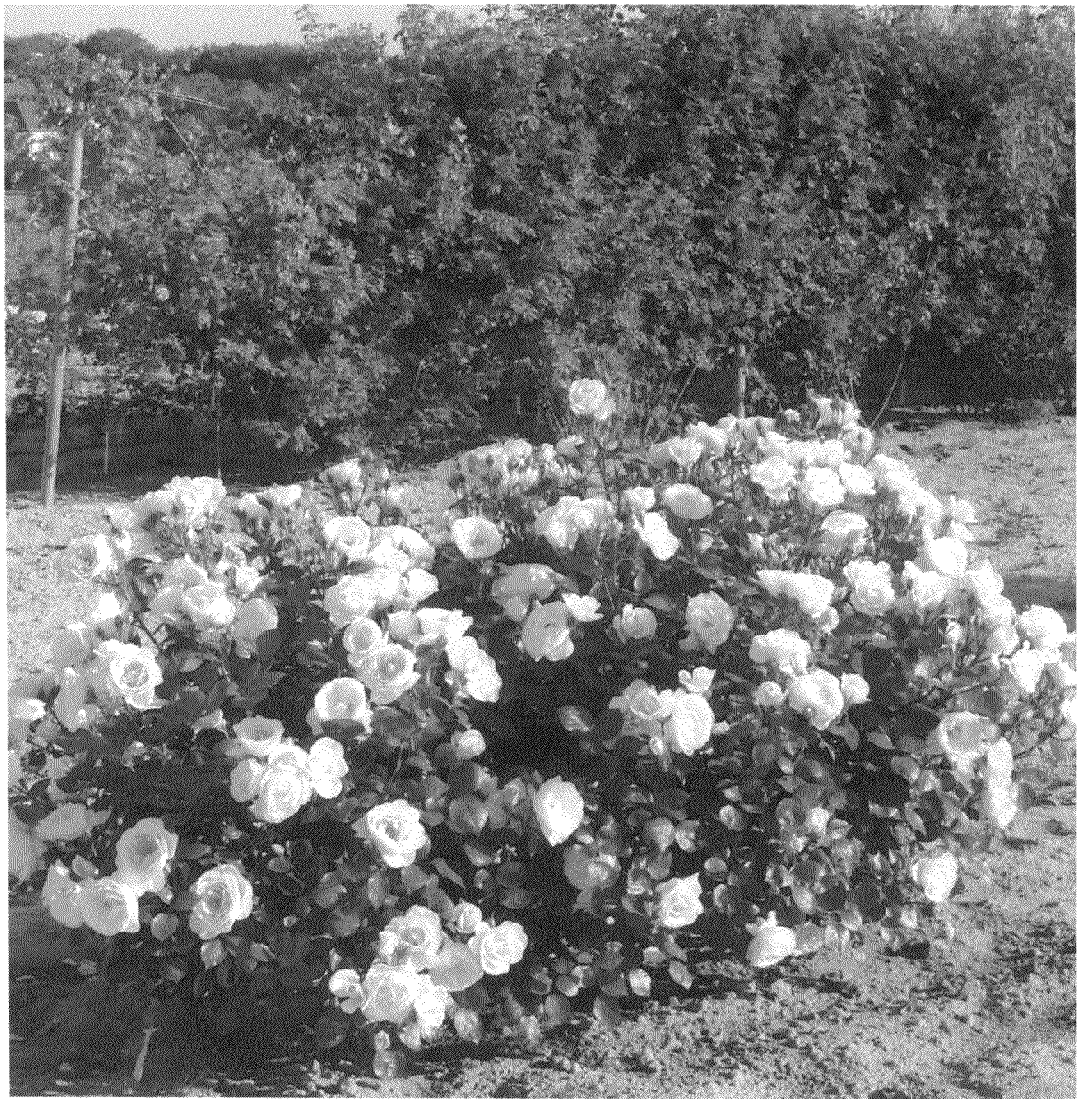

The photograph of FIG. 1 shows two plants of the new variety of rose, placed side by side in field, in blossom during June.

Figure 2:
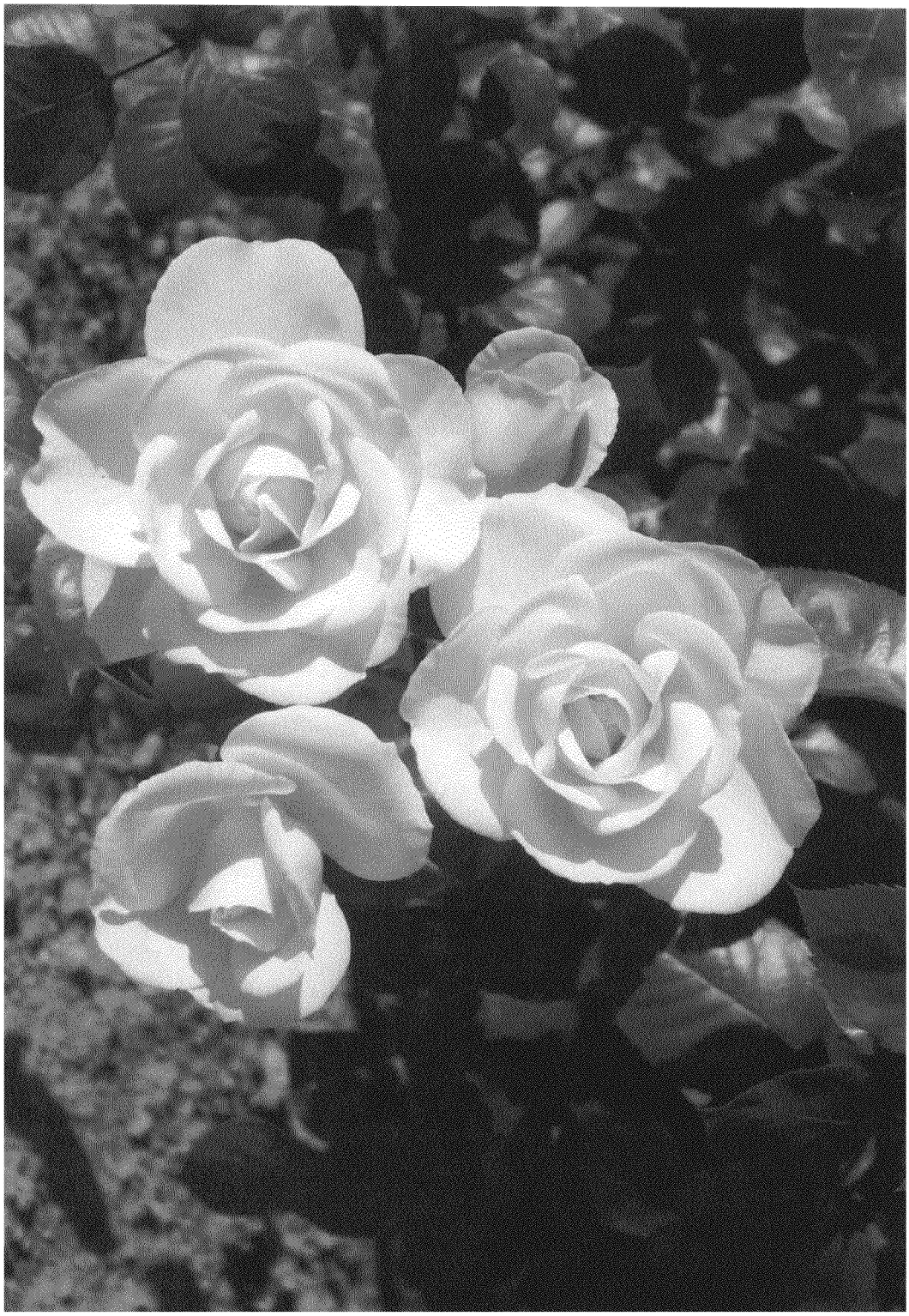

The photograph of FIG. 2 shows four flowers of the new variety, aged from 2 to 4 days.

Figure 3:
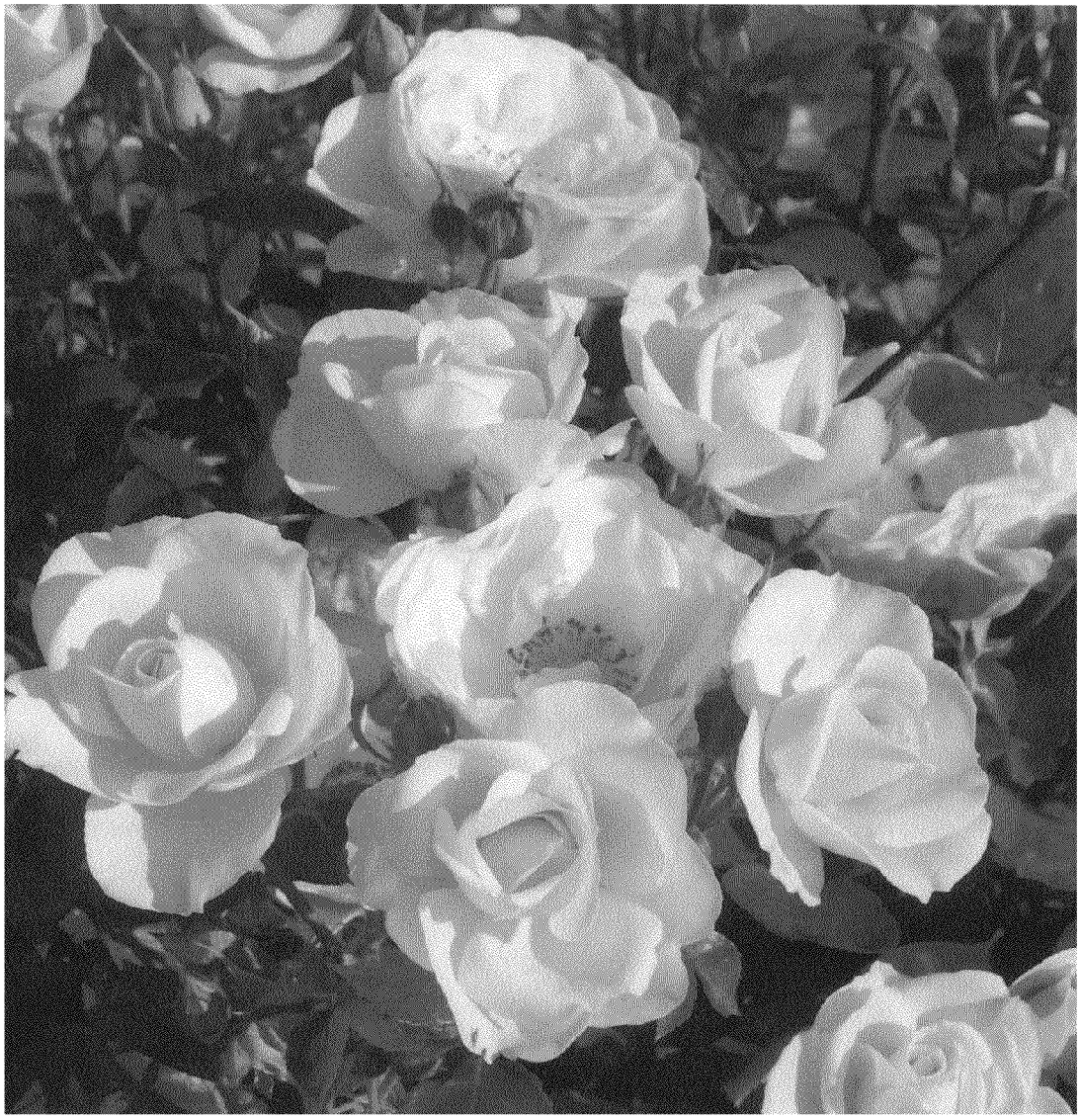

The photograph of FIG. 3 shows also four spread flowers, the oldest of which is 5 days old and lets appear its reproductive organs.

Figure 4:
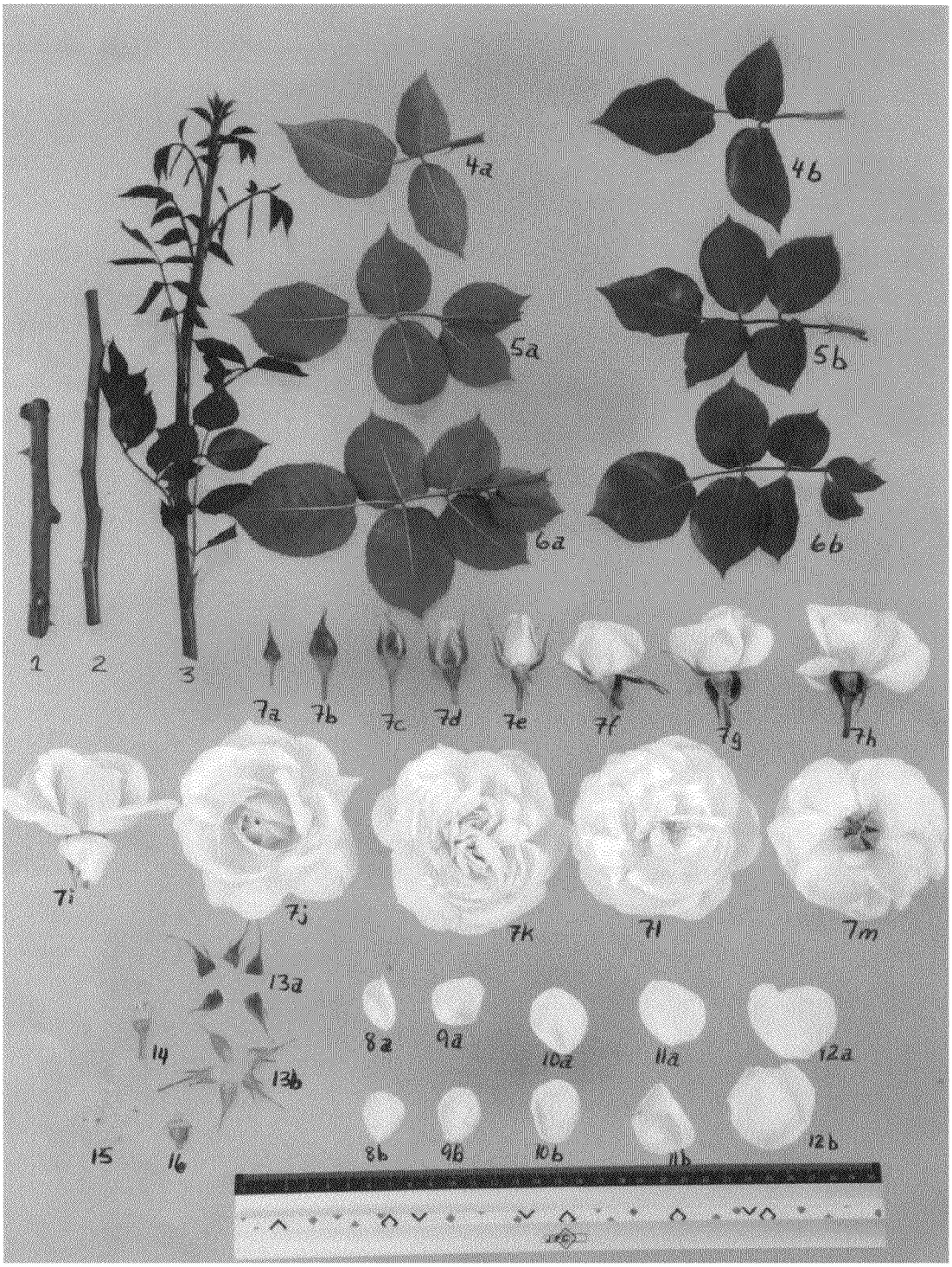

The photograph of FIG. 4 presents different parts of the new variety of rose. These parts are the following. Reference 1 is a twig of two years. Reference 2 is a twig of the year. Reference 3 is a young shoot. References 4 to 6 are leaves, presented respectively by their under surface 4a 5a 6a and their upper surface 4b 5b 6b. References 7a to 7m show the various stages of the blooming of the flower of the new variety. From reference 7e to reference 7m the time is approximately 6 days. References 8 to 12 are petals of the same three days old flower, presented respectively by the external surface 8a to 12a and their inner side surface 8b to 12b. Petals situated to the left on the figure, of a slightly darker color, corresponding to those of the center of the flower, petals situated on the right of the figure being those of the periphery of the flower. Reference 13 are sepals, 13a being the lower surface of sepals, 13 b being their upper surface. Reference 14 shows the stamens, 15 pollen and 16 pistils. In addition on this FIG. 4, a scale in centimeters is shown.

DETAILED DESCRIPTION

The chart used in the identification of the colors is that of The Royal Horticultural Society (R.H.S. Colour Chart) except where ordinary color terms are utilized. Such common color terms are to be accorded their customary dictionary significance.

The description is based upon the observation of plants of the new variety at an age of approximately three years during the month of June while being grown in the field at Pithiviers near Orleans (France)

Class: Floribunda.

Plant:

*Growth habit.*—Vigorous, rounded and bushy.

*Blooming habit.*—Abundant and substantially continuous.

*Height.*—Commonly approximately 2.6 to 3.3 feet at maturity.

*Width.*—Commonly approximately 2 to 2.6 feet at maturity.

Branches:

*Color.*—Young stems: commonly near Greyed-Purple Group 183B. Adult wood: commonly near Yellow-Green Group 146A.

*Length.*—Commonly approximately 60-80 cm.

*Diameter.*—Commonly approximately 9 mm at the base.

*Internode length.*—Commonly approximately 4 to 4.5 cm.

*Grafted.*—Rootstock is *rosa corymbifera* 'laxa'.

Thorns:

*Size.*—Commonly approximately 7 mm in length on average when immature, and approximately 7 mm in length on average when mature.

*Color.*—Commonly near Greyed-Purple Group 183B with bronze coloration when immature, and near Greyed-Orange Group from 176B to 165A when mature.

*Shape.*—Upper edge: concave. Under edge: convex. Thornprint: elliptic.

*Quantity.*—Few, located only at the base of the stems over 15 to 30 cm.

Leaves: Overall appearance.—Attractive dark green.

Leaflets:

*Shape of base of terminal leaflet.*—Obtuse to rounded.

*Leaflet cross section.*—Slightly concave.

*Leaflet ondulation of margin.*—Weak.

*Number.*—3, 5, and 7 per leaf. Average size of a complete leave: 14.5 cm, range from 13 to 18 cm. Average width of a complete leave: 11 cm, range from 9 to 13 cm. Average size of the terminal leaflets commonly approximately 6.5 cm in length on average, and approximately 4.5 cm in width at the widest point.

*Serration.*—Medium, irregular.

*Texture.*—Thick.

*Color* (*young foliage*).—On the upper surface commonly near Greyed-Red Group 179A with tones of near Greyed-Purple Group 183A going to green bronze, and on the under surface commonly near Greyed-Purple Group 183A going to grayish brown 166 A.

*Color* (*adult foliage*).—On the upper surface near Green Group 147A, and on the under surface near Green Group 146A to B.

Stipules:

*Shape.*—Commonly turn outward at an angle greater than 45 degrees and often recurve toward the stem.

*Length.*—Commonly approximately 1.6 to 2 cm.

*Width.*—Commonly approximately 4 to 6 mm.

*Color.*—Inside near Green Group 146B with reddish nervure. Outside: 146B with green bronze nervure.

Petiole:

*Length.*—Commonly approximately 2.4 cm, range from 1.9 to 2.9 cm.

*Diameter.*—commonly approximately 2 mm.

*Color on floral stems.*—Upper surface: Green Group 137B with sometimes reddish coloration in the middle. Under surface: Green Group 146C with sometimes green bronze coloration in the middle.

Rachis:

*Length.*—Commonly approximately 4.3 cm, range from 3 to 5.5 cm.

*Color.*—Near Green Group 146B.

Inflorescence:

*Number of flowers.*—Typically in clusters of three to five flowers and commonly with up to 40 or more open blossoms being present on an individual plant at one time.

*Peduncle.*—Commonly approximately 3 to 5.5 cm in length on average, commonly approximately 4 mm in diameter on average, and near Green Group 146B in coloration.

*Sepals.*—Number: five. Shape: generally lanceolate. Apex: acute. Base: truncate. Margin: mostly entire for two and slightly incised towards the apex for the others. Size: commonly approximately 2.6 cm in length on average, range from 2.5 to 3 cm, and approximately 6 mm in width on average at the widest point. Texture: smooth on both surfaces. Color: on the upper surface commonly near Green Group 146B, to 146C, and on the under surface commonly near grayed-red group 178B going to grayed-purple group 183C.

*Buds as first petals open* (*excluding terminal flower*).—Shape: ovoid and pointed. Length: approximately 3 cm on average, range from 2.7 to 3.2 cm. Width: approximately 5 cm on average at the widest point, range from 4 to 6 cm. Color as calyx breaks: commonly near Red-Purple Group 62B to 62C.

*Flower.*—Form: double. View from above: rounded. Side view of upper part: flattened convex. Side view of lower part: flat to concave. Diameter: approximately 8.7 cm on average, range from 7.5 to 9.5 cm.

*Color* (*when opening begins*).—Upper surface: commonly Red-Purple Group 65B to 65C. Under surface: commonly Red-Purple Group 62D.

*Color* (*at end of blooming*).—Upper surface: commonly between Red-Purple Group 69B and 69C. Under surface: commonly between Red-Purple Group 69C and 69D.

*Fragrance*.—Light, powdered, with fresh herbal notes.

*Lasting quality*.—The blossoms commonly last approximately 7 days on average on the plant depending upon environmental conditions, and approximately 2 to 3 days on average when cut and placed in a vase.

*Petal length* (*excluding terminal flower. Second row from outside*.—Commonly approximately 4 cm, range from 2.5 to 5.5 cm.

*Petal width* (*same conditions as length*).—Commonly approximately 4 cm, range from 2.5 to 5.7 cm.

*Petal shape*.—Obovale large.

*Petal reflexing of margin*.—Slightly reflexing.

*Petal undulation of margin*.—Weak to medium.

*Petal crenelage of margin*.—None.

*Petal texture*.—Smooth on both surfaces.

*Petal number*.—Approximately 26 on average under normal growing conditions, range from 22 to 32.

*Petal drop*.—Good with the petals commonly detaching cleanly before drying.

*Stamen number*.—Approximately 120 to 140 on average.

*Anthers*.—Coloration commonly Yellow-Orange Group 15C.

*Filaments*.—Commonly approximately 4 to 6 mm in length on average, and near Yellow Group 4C to 4d in coloration.

*Pollen*.—Commonly formed in a sparse quantity.

*Pistils*.—Separate and free, and approximately 60 in number on average.

*Styles*.—Commonly approximately 5 mm in length on average, and near Yellow Group 2C at the base in coloration, becoming red orange near the stigmas Yellow Group 34B.

*Stigmas*.—Commonly approximately 1 mm in diameter, and near Yellow Group 6D in coloration.

*Receptacle*.—Generally ovoid in shape, approximately 5 mm in length.

*Hips*.—Pitcher shaped.

Development:

*Vegetation*.—Vigorous and strong.

*Blooming*.—Abundant and substantially continuous.

*Resistance to diseases*.—During observations to date, average resistance with respect to Black Spot, Mildew, and Rust.

I claim:

1. A new and distinct Floribunda rose plant characterized by the following characteristics: (a) exhibits a rounded and bushy growth habit, (b) forms strong and vigorous vegetation, (c) abundantly and substantially continuously forms attractive double light pink blossoms, (d) displays attractive ornamental glossy dark green foliage, and (e) is particularly well suited for providing attractive ornamentation; substantially as shown and described.

* * * * *